US008383037B2

(12) United States Patent
Burke

(10) Patent No.: US 8,383,037 B2
(45) Date of Patent: Feb. 26, 2013

(54) GAMMA HARDENED PHARMACEUTICAL DEVICES

(75) Inventor: Aaron Burke, Hamilton, MA (US)

(73) Assignee: EMD Millipore Corporation, Billerica, MA (US)

(*) Notice: Subject to any disclaimer, the term of this patent is extended or adjusted under 35 U.S.C. 154(b) by 0 days.

(21) Appl. No.: 13/414,884

(22) Filed: Mar. 8, 2012

(65) Prior Publication Data

US 2012/0171075 A1 Jul. 5, 2012

Related U.S. Application Data

(62) Division of application No. 12/502,259, filed on Jul. 14, 2009.

(60) Provisional application No. 61/190,049, filed on Jul. 16, 2008.

(51) Int. Cl.
*A61L 2/00* (2006.01)

(52) U.S. Cl. ........................................................ 422/22

(58) Field of Classification Search .................... 422/22
See application file for complete search history.

(56) References Cited

U.S. PATENT DOCUMENTS

| 7,048,775 | B2 | 5/2006 | Jornitz et al. | |
| RE39,361 | E | 10/2006 | Den Dekker et al. | |
| 7,259,675 | B2 | 8/2007 | Baker et al. | |
| 8,007,568 | B2 | 8/2011 | DiLeo et al. | |
| 2004/0222358 | A1* | 11/2004 | Bui et al. | 250/214.1 |
| 2005/0148819 | A1 | 7/2005 | Noguchi et al. | |
| 2006/0055001 | A1* | 3/2006 | Fujii | 257/619 |
| 2007/0059442 | A1* | 3/2007 | Sabeta | 427/142 |
| 2007/0240578 | A1 | 10/2007 | DiLeo | |
| 2007/0243113 | A1 | 10/2007 | DiLeo | |
| 2009/0050814 | A1 | 2/2009 | Seefeldt et al. | |
| 2009/0202387 | A1* | 8/2009 | Dlugos et al. | 422/22 |
| 2010/0017159 | A1 | 1/2010 | Burke | |
| 2012/0163411 | A1 | 6/2012 | Burke | |

FOREIGN PATENT DOCUMENTS

| EP | 2087913 A1 | | 8/2009 |
| JP | 01-108191 | * | 4/1989 |
| WO | WO2008061313 | * | 5/2008 |
| WO | 2009/017612 A2 | | 2/2009 |

OTHER PUBLICATIONS

Schwank, et al, "Radiation Effects in SOI Technologies", Jun. 2003, IEEE Transations on Nuclear Science, vol. 50, No. 3, p. 522-538.*
Office Action mailed Aug. 21, 2012 in corresponding U.S. Appl. No. 12/502,259.
IEEE Transactions on Nuclear Science, vol. 50, No. 6, Dec. 2003, pp. 2310-2315, "Total Dose Hardness Assurance Testing Using Laboratory Radiation Sources", Paillet, et al.
Honeywell, Solid State Electronics Center, XP 002548312, [online] Mar. 29, 2006, "Rad Hard Aerospace Components Products", 1 page.

(Continued)

*Primary Examiner* — Walter D Griffin
*Assistant Examiner* — Christopher Vandeusen
(74) *Attorney, Agent, or Firm* — Nields, Lemack & Frame, LLC

(57) ABSTRACT

A system and method for implementing embedded electronics in environments where radiation or extreme temperatures are used is disclosed. Embedded electronics are affixed to various components of a pharmaceutical system, thereby enabling the customer to download pertinent information about the component, such as lot number, date of manufacturer, test parameters, etc. Additionally, these electronics allow an array of functions and features to be implemented, such as integrity tests and diagnostics. The electronics in the pharmaceutical components utilize a technology that is not as susceptible to radiation and extreme temperatures as traditional electronics.

10 Claims, 8 Drawing Sheets

OTHER PUBLICATIONS

Journal of Microelectromechanical Systems, vol. 17, No. 6, Dec. 2008, pp. 1408-1417, "Tungsten-Based SOI Microhotplates for Smart Gas Sensors", Syed, et al.

Aerospace Conference, 2005 IEEE, Mar. 5, 2005, XP 031213646, pp. 1-13, "1/f Noise and DC Characterization of Partially Depleted SOI N-and P-MOSFETs from 20 degrees C-250 degrees C", Ericson, et al.

International Search Report mailed Oct. 27, 2009 in corresponding PCT application No. PCT/US2009/050445.

International Search Report and Written Opinion mailed Dec. 29, 2009 in corresponding PCT application No. PCT/U52009/050445.

Office Action—Restriction—mailed Feb. 16, 2012 in corresponding U.S. Appl. No. 12/502,259.

Office Action mailed Mar. 22, 2012 in corresponding U.S. Appl. No. 12/502,259.

* cited by examiner

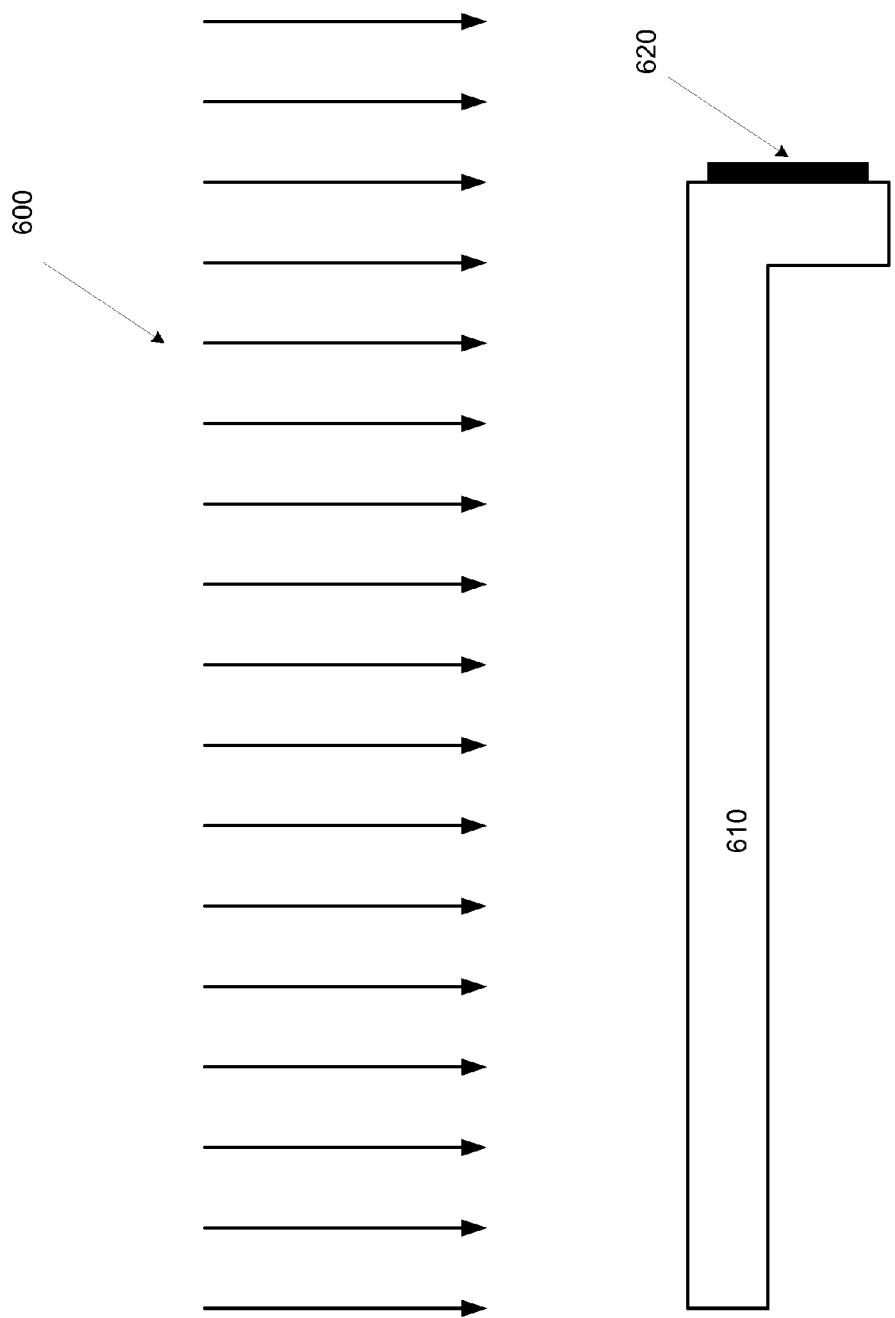

GAMMA HARDENED PHARMACEUTICAL DEVICES

This application is a divisional of U.S. patent application Ser. No. 12/502,259 filed Jul. 14, 2009, which claims priority of U.S. Provisional Patent Application Ser. No. 61/190,049, filed Jul. 16, 2008, the disclosures of which are herein incorporated by reference in its entirety.

BACKGROUND OF THE INVENTION

The use of electronics in pharmaceutical devices has become prevalent, especially in the management of assets, particularly those applications associated with inventory management. For example, the use of RFID tags permits the monitoring of the production line and the movement of assets or components through the supply chain. Additionally, these electronics allow more functionality to be embedded in the devices. Such functions as integrity testing, calibration and diagnostics, can now be performed in situ because of the use of these embedded electronics.

To further illustrate one such use of embedded electronics, a manufacturing entity may affix RFID tags to components as they enter the production facility. These components are then inserted into the production flow, forming sub-assemblies in combination with other components, and finally resulting in a finished product. The use of RFID tags allows the personnel within the manufacturing entity to track the movement of the specific component throughout the manufacturing process. It also allows the entity to be able to identify the specific components that comprise any particular assembly or finished product.

In addition, the use of RFID tags has also been advocated within the drug and pharmaceutical industries. In February 2004, the United States Federal and Drug Administration issued a report advocating the use of RFID tags to label and monitor drugs. This is an attempt to provide pedigree and to limit the infiltration of counterfeit prescription drugs into the market and to consumers.

Since their introduction, RFID tags have been used in many applications, such as to identify and provide information for process control in filter products. U.S. Pat. RE39,361, reissued to Den Dekker in 2006, discloses the use of "electronic labels" in conjunction with filtering apparatus and replaceable filter assemblies. Specifically, the patent discloses a filter having an electronic label that has a read/write memory and an associated filtering apparatus that has readout means responsive to the label. The electronic label is adapted to count and store the actual operating hours of the replaceable filter. The filtering apparatus is adapted to allow use or refusal of the filter, based on this real-time number. The patent also discloses that the electronic label can be used to store identification information about the replaceable filter.

U.S. Pat. No. 7,259,675, issued to Baker et al, in 2007, discloses a process equipment tracking system. This system includes the use of RFID tags in conjunction with process equipment. The RFID tag is described as capable of storing "at least one trackable event". These trackable events are enumerated as cleaning dates, and batch process dates. The publication also discloses an RFID reader that is connectable to a PC or an internet, where a process equipment database exists. This database contains multiple trackable events and can supply information useful in determining "a service life of the process equipment based on the accumulated data". The application includes the use of this type of system with a variety of process equipment, such as valves, pumps, filters, and ultraviolet lamps.

RFID tags are but one use of embedded electronics as used in pharmaceutical devices. U.S. Pat. No. 7,048,775 issued to Jornitz et al in 2006, discloses a device and method for monitoring the integrity of filtering installations. This publication describes the use of filters containing an onboard memory chip and communications device, in conjunction with a filter housing. The filter housing acts as a monitoring and integrity tester. That application also discloses a set of steps to be used to insure the integrity of the filtering elements used in multi-round housings. These steps include querying the memory element to verify the type of filter that is being used, its limit data, and its production release data.

Other patent applications have also disclosed the use of embedded sensors to aid in diagnostics or in situ integrity tests.

Despite the improvements that have occurred through the use of embedded electronics in pharmaceutical devices, there are additional areas that have not been satisfactorily addressed. For example, to date, embedded electronics and RFID tags cannot be employed in environments that require or utilize radiation. This is due to the fact that most electronic devices, and particularly memory storage devices, cannot withstand radiation. When subjected to radiation, specifically gamma and beta radiation, the contents of these memory elements are corrupted, thereby rendering them useless in this environment. Additionally, certain other electronic components, such as integrated circuits, fail when subjected to radiation. The most common failure mode is a condition commonly referred to as "latchup". However, there are a number of applications, such as, but not limited to, the drug and pharmaceutical industries, where radiation of the system is a requirement. Furthermore, many electronic components cannot withstand temperature extremes, such as temperatures above 125° C. or below −55° C. These extreme temperatures are used in the pharmaceutical industry to sterilize materials, and to store finished product. Therefore, it would be extremely beneficial to these industries and others, to have embedded electronics that could withstand radiation and/or extreme temperature ranges without data loss or corruption.

SUMMARY OF THE INVENTION

The shortcomings of the prior art are overcome by the present invention, which describes a system and method for implementing embedded electronics in environments where radiation or extreme temperatures are used. Embedded electronics are affixed to various components of a pharmaceutical system, thereby enabling the customer to download pertinent information about the component, such as lot number, date of manufacturer, test parameters, etc. Additionally, these electronics allow an array of functions and features to be implemented, such as integrity tests, sensing of various parameters such as temperature, pH, conductivity, pressure and the like and diagnostics. The electronics in the pharmaceutical devices utilize a technology that is not as susceptible to radiation and extreme temperatures as traditional electronics.

BRIEF DESCRIPTION OF THE DRAWINGS

FIG. 6b shows a second orientation of a bag and attached semiconductor; and

DETAILED DESCRIPTION OF THE INVENTION

The use of miniature and embedded electronics has become more and more prevalent. However, in certain applications, their use is limited, or not possible. For example, any environment in which the electronics must be subjected to radiation will corrupt or destroy the physical device, or may alter the state of the device. Therefore, devices that are gamma or beta irradiated, such as pharmaceutical components, or subject to x-rays, such as devices that pass through airport security systems, currently cannot easily utilize electronic circuits. Thus, products used in these environments must find alternative solutions. For example, in some cases, the electronics are eliminated and a simple barcode is affixed to the device, and a database is used to store and retrieve the pertinent information associated with that barcode. In other words, the memory element of the tag is literally removed and kept elsewhere. While this allows the data associated with the device to be saved and retrieved, it requires computer access and a remote database for storage. This solution is further complicated when the device manufacturer and the device user both want to access and update the associated information. Such an arrangement requires joint access to the database, which may be difficult or impossible due to the need for confidentiality and data protection.

A second solution involves affixing the embedded electronics at a point in the process after the irradiation of the device. For example, pharmaceutical components are often subjected to gamma or beta radiation. Application of the electronic devices after this step can bypass the memory corruption and circuit malfunction issues described above. However, data associated with that component which was created before the radiation step must be somehow saved and associated with the appropriate component, so that the later affixed electronics contains all of the required information. Additionally, the electronic device must itself undergo some sterilization process before it can be affixed to the pharmaceutical device.

A third solution is to prohibit the use of radiation with the device. Thus, users must find an alternate approach to achieve the results sought by irradiating the device (such as high temperature steam sterilization). However, sterilization, such as by autoclave, requires temperatures typically in excess of 145° C. Military grade integrated circuits, which are more costly than standard commercial grade equivalents, are typically only rated to 125° C. Thus, steam sterilization also potentially can damage the electronics. Obviously, none of these solutions is optimal.

Figure 1:
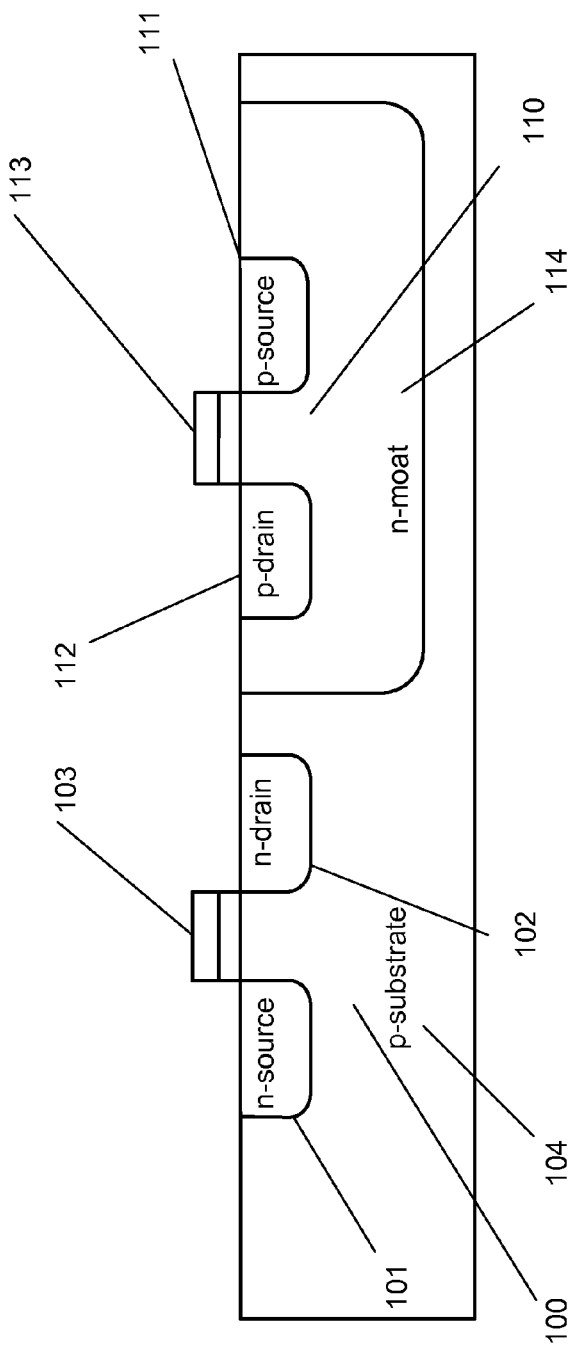
FIG. 1 shows a cross-section of a traditional semiconductor substrate.
Figure 2:
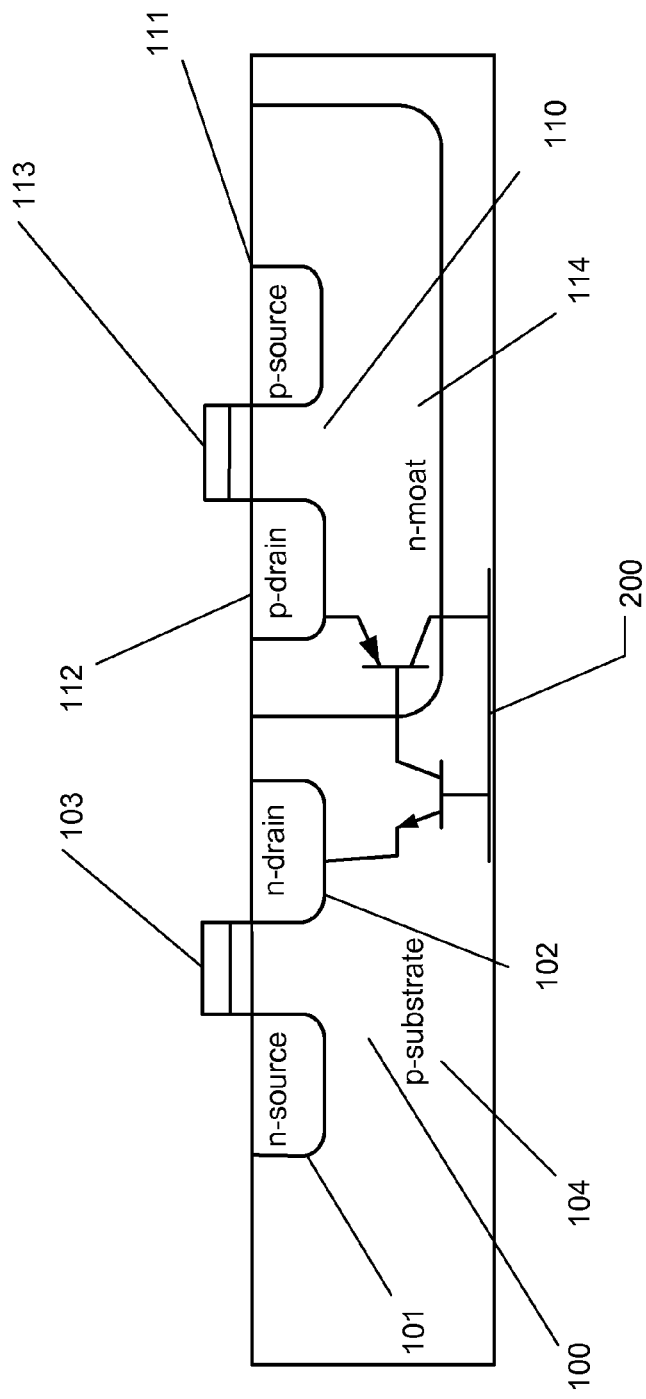
FIG. 2 shows the phenomenon that causes latchup in the substrates of FIG. 1.

At the root of the problem is the inability for a traditional semiconductor device to withstand sterilization, such as by gamma or beta radiation or steam sterilization. This is a very well known problem, and affects all types of CMOS semiconductor devices, including transistors, memory circuits, amplifiers, power conversion circuits, and analog/digital and digital/analog converters. FIG. 1 shows the typical structure for a CMOS device. The N channel MOSFET 100 comprises a N-type source 101 separated from an N-type drain 102. The gate 103 is located between these two N-type regions. The substrate 104 around the MOSFET is p-type. The P channel MOSFET 110 comprises a P-type source 111 separated from a P-type drain 112. The gate 113 is located between these two P-type regions. The substrate around the MOSFET is n-type moat or well 114. When exposed to radiation, these CMOS devices typically fail in such a way that both the NMOS transistor 100 and its complementary PMOS transistor 110 both turn on, effectively creating a SCR 200 (silicone controlled rectifier) or thyristor. These devices are essentially N—P—N—P devices, which, once turned on, can only be turned off by the removal of power from the device. Typically, the SCR is created between the p-drain 112, n-moat 114, p-substrate 104 and n-drain 102 of the adjacent transistor, as shown in FIG. 2. Thus, the activation of this SCR creating a short circuit between the power rails of the CMOS device, which persists until the power is removed from the device. Although this problem most often occurs between power rails, other short circuits within the device are also possible. Failure to mitigate this failure can lead to permanent damage.

Other semiconductor fabrication techniques are known to exist. One such technique is known as Silicon-on-Insulator (or SOI). SOI fabrication has been in use for about 10 years. Companies, such as Honeywell and Cissoid, have commercialized circuit components necessary to assemble wireless communication devices as well as basic sensor circuits and amplifiers. Typically, integrated circuits made using SOI techniques are resistant to junction temperatures up to 225° C., well in excess of current military standards available for traditional CMOS devices. For example, traditional integrated circuits are typically specified for two maximum temperatures; operational and storage. Most standard integrated circuits have a maximum storage temperature of 150° C., and a maximum operating temperature of 125° C. In contrast, SOI based integrated circuits are commonly rated at 225° C. operating temperature.

Figure 3:
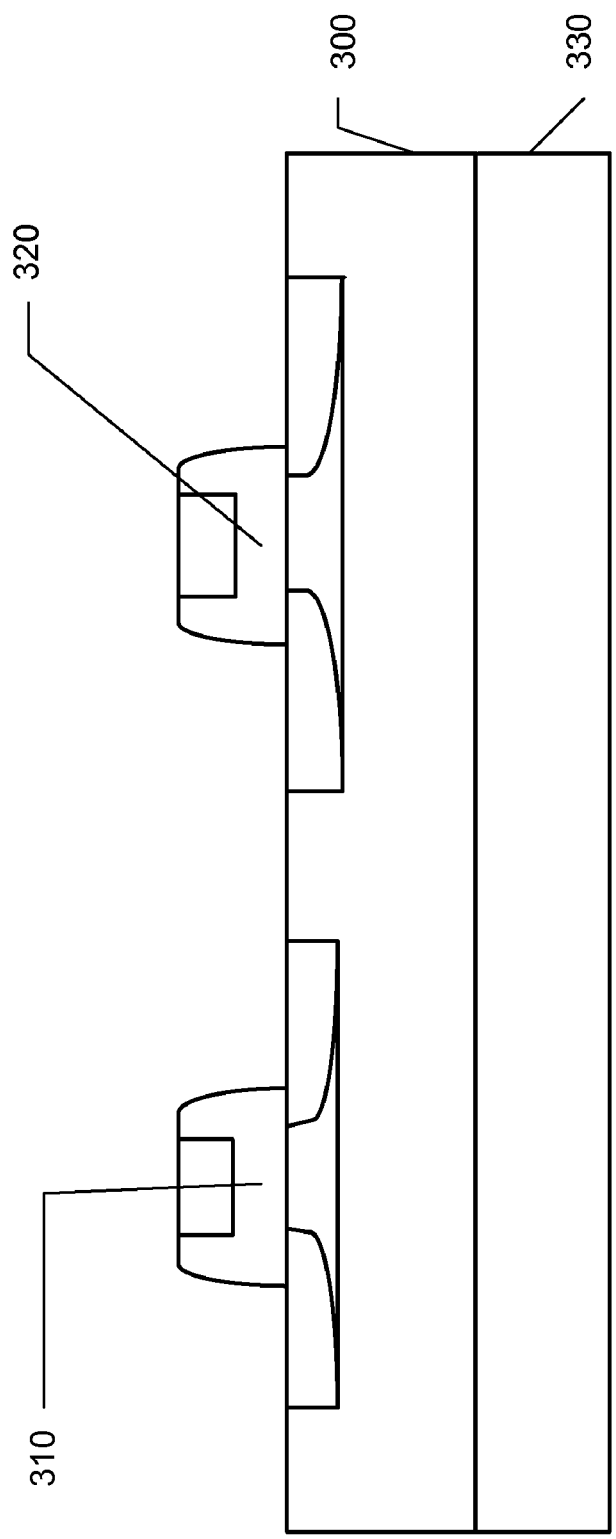
FIG. 3 shows a cross-section of a Silicon on Insulator (SOI) substrate.

In contrast to traditional semiconductors, insulating material 300, such as silicon dioxide ($SiO_2$), aluminum oxide ($Al_2O_3$) or other suitable materials, separates the various transistors from one another and from the bulk substrate 330. FIG. 3 shows a cross-section of a typical SOI device. Note that the presence of the insulating material 300 between the transistors 310,320 prohibits the formation of the SCR device described above, thereby mitigating the possibility of latch-up in these devices. In addition, the insulating material isolates the transistors 310,320 from the doped substrate 330.

As stated above, pharmaceutical devices need to be sterilized. The most common forms of sterilization include gamma or beta radiation, and high temperature steam sterilization, both of which are impossible with traditional semiconductor devices.

Currently, the pharmaceutical industry is pursuing the use of disposable components. Typically, these parts are manufactured by the pharmaceutical company and then shipped to the customer. Often, the customer assembles these disposable components into a complete system, which they may then sterilize before use. Such disposable systems include the MOBIUS® line of products manufactured by Millipore Corporation.

Many of these disposable products benefit because of the advantages listed above. For example, through the addition of embedded electronics. For example, RFID tags can be read and rewritten by the manufacturer and/or customer to allow improved inventory processes. Based on this, it is possible to develop a sophisticated pharmaceutical asset management system. In one embodiment, the pharmaceutical components, such as filtration devices, hoses and the like, have a remotely readable tag affixed to them, such as an RFID tag. This tag contains device specific information, such as, but not limited to device specific information (such as serial number, date of manufacture, etc.), device specifications (such as upper and lower pressure limits), and device test parameters. Customers could use this information in a variety of ways. For example, an automated instrument setup and calibration procedure can be established. By using an RFID or equivalent reader, the customer could determine calibration values, upper and lower limits, units of measure and/or the data exchange protocol.

This semiconductor technique can also be used to create other embedded electronic components that can withstand sterilization, such as pressure, temperature and concentration sensors. It is desirable to use sensors to measure fluid conditions, such as temperature, pressure and flow rate. It is also desirable to measure fluid components, such as by using a chemical or concentration sensor. The use of some of these types of sensors is described in U.S. patent application Ser. Nos. 11/402,737, 11/402,437, and 11/402,438, the disclosure of each is hereby incorporated by reference. In these cases, information obtained by the sensors can be stored in embedded memory and read by the customer at a later time. Alternatively, the sensor data can be transmitted wirelessly to a remote transmitter or receiver.

Figure 4:
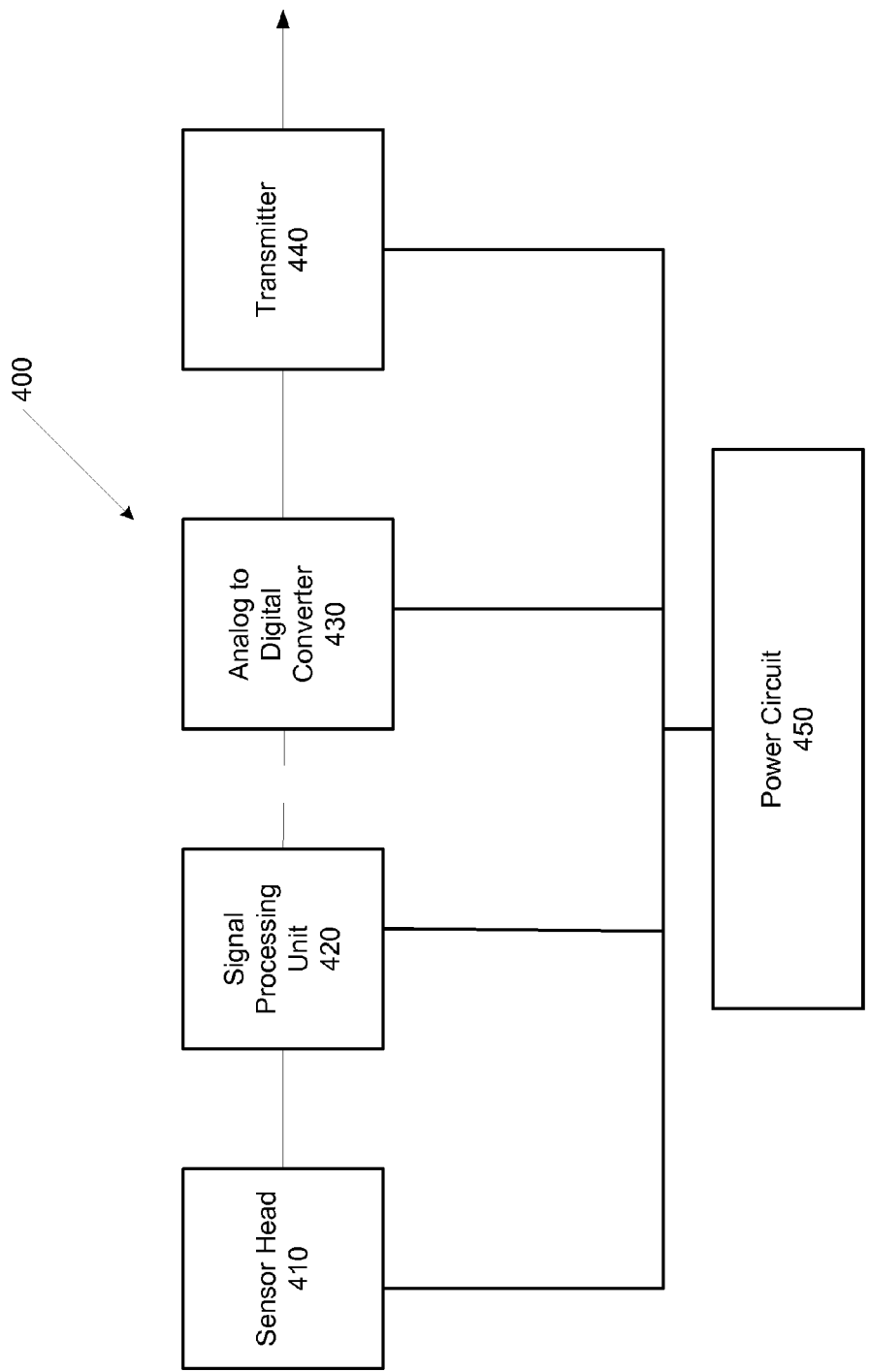
FIG. 4 shows a block diagram of a sensor.

Sensors 400 are typically made up of a number of subcomponents, as shown in FIG. 4. There is a sensor head 410, which is the portion of the sensor that converts the physical characteristic, such as pressure or temperature, to an electrical signal. This signal can be a voltage, a current, a resistance, or any other electrical quantity. The sensor body is typically made up of a number of subcomponents, such as a signal processing unit 420, an analog to digital converter 430, a transmitter 440 and a power circuit 450.

The output from the sensor head may be passed to a signal processing unit 420. This unit 420 may perform a number of different functions. For example, this unit 420 may scale the incoming signal to change the input range into a different output range. For example, an incoming signal may be in the range of 0-100 mV, whereas the desired output is between 100 mV and 1V. The signal processing unit 420 would translate and scale the incoming voltage to achieve the desired output range.

Alternatively, the signal processing unit 420 may add compensation for thermal drift or other variables. For example, a pressure sensor may experience an offset based on the ambient temperature. The signal processing unit 420 can compensate for such an error.

In addition, the signal processing unit 420 may adjust the received signal based on known process variation. For example, devices may vary for each production lot. This variation may be determined by a tester, which then records the required compensation value in the signal processing unit 420. This value may be added to the output, or may be a scaling factor.

Additionally, the signal processing unit 420 may include means for calibration. In this case, the signal processing unit 420 may include means to test the process variation and thermal drift. It then performs a calibration test to determine these factors and uses them to appropriately adjust the received electrical signal.

A third subcomponent of a sensor may be an analog to digital converter 430. Typically, the sensor head 410 produces an analog output, as a voltage, current or resistance. This output may need to be converted to a digital value. This is typically accomplished through the use of an analog to digital converter 430. This analog to digital converter 430 may receive the output of the signal processing unit 420. Alternatively, it may receive the output of the sensor head 410 and supply a digital value to the signal processing unit 420. In a third embodiment, the analog to digital converter 430 is located within the signal processing unit 420 and converts the signal after unit has been partially processing by the signal processing unit 420.

A fourth subcomponent is a transmitter 440. In some embodiments, the transmitter 440 is simply a wire, which connects the sensor components to an external reader. In other embodiments, the transmitter 440 may be wireless. A wireless transmitter may utilize any protocol, and the disclosure is not limited to any particular embodiment. For example, protocols such as the ZIGBEE® protocol, 802.15.1, 802.15.4, RFID, the BLUETOOTH® protocol and others, are suitable for this application.

A fifth subcomponent of a sensor 400 is the power circuit 450. This circuit 450 provides the required power to the rest of the sensor 400. In some embodiments, a battery is used as the energy source. In other embodiments, wireless induction is used to supply energy to the sensor. In addition to supplying energy, the power circuit 450 transforms that energy into the required voltages, typically through the use of rectifiers, zener diodes, capacitors, and other components.

In some embodiments, as is described in more detail below, the above described sensor 400 is at least partially made using SOI technology. For example, in some embodiments, the entire sensor is made using SOI technology. In other embodiments, only certain subcomponents are made using SOI technology.

For example, in some embodiments, the signal processing unit 420, which may include integrated circuits, is made using SOI technology.

Figure 5:
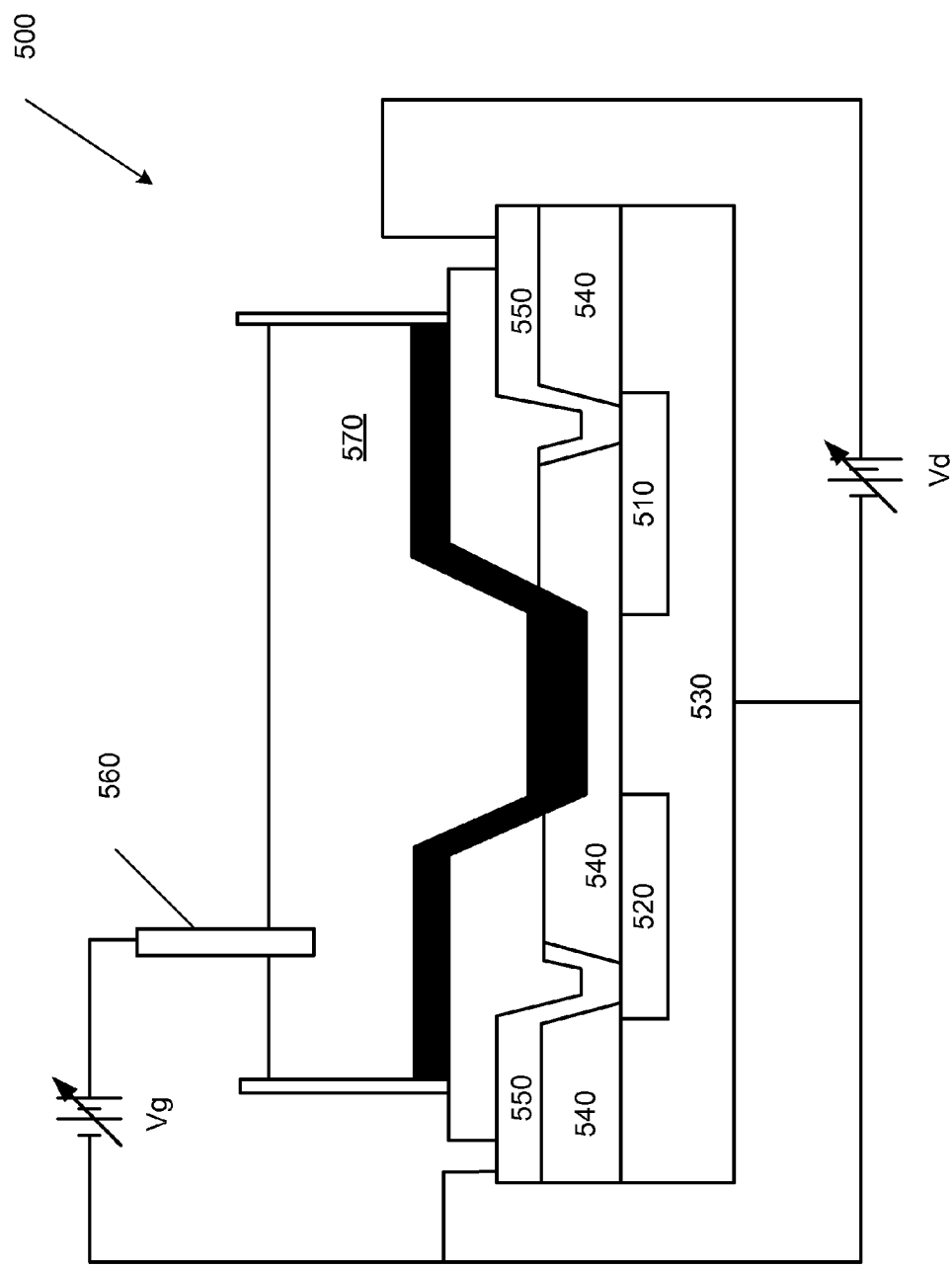
FIG. 5 shows a cross-section of an ISFET.

In other embodiments, the sensor head 410 is made using SOI technology. For example, ISFETs can be used in the creation of concentration sensors. These ISFETs utilize drain and source regions analogous to those found in a MOSFET. FIG. 5 shows an ISFET 500 made using SOI technology. Like traditional MOSFETS, the ISFET has an n-type drain region 510 and an n-type source region 520. Both regions are located within a p-type substrate 530, such as silicon. An insulator 540 is then layered on top of the p-type silicon 530, the source 520 and the drain 510, leaving only a small area on the source and drain regions for connection to the metal contacts 550. The metal gate traditionally used for a MOSFET is replaced by an electrode 560 spaced apart from the device. The ions in the solution 570 provide the electrical path from the electrode 560 to the device. Thus, the concentration of electrons determines the strength of that electrical path, and therefore the amount that the FET is enabled.

Other examples of a sensor head using SOI technology are the use of LEDs or photodiodes. These LEDs can be used to detect concentration density when used with fluorescent materials, and can also be made using SOI technology.

Additionally, SOI technology is suitable for other devices, including amplifiers, analog-to-digital converters, digital-to-analog converters, digital logic, radio frequency components, power conversion circuitry and memory devices.

Finally, the ability to utilize a remotely readable asset management tag is beneficial for pharmaceutical consumables, such as filters, bags, tubes and process instruments. Currently, the pharmaceutical industry is exploring the use of disposable technology. In this scenario, the customer could configure their required system using at least some disposable components (such as filters, bags, hoses, etc). This allows the customer to customize their configuration as necessary and also eliminates the costly cleaning operations that must currently be performed. To improve the efficiency and predictability of using disposable components, RFID tags can be affixed to these components. Such tags allow for the wireless automated identification of components, including such information as catalog number, serial number, and date of manufacture. These tags also allow a secure automated method of transferring unit specific specification to the customer as noted above. Using the information contained within these tags, a GAMP compliant method of transferring unit specific test procedure information to an automated integrity tester can be created. The semiconductor devices described above are beneficial in this application, since these disposable components must be irradiated to insure sterilization. Furthermore, in addition to storage and wireless communications that can be provided by RFID tags, other functions are also possible given the use of SOI technology.

There are various applications where this SOI technology would be beneficially employed. Currently, there are some disposable pharmaceutical components that employ sensors. Due to the issues associated with sterilization described above, many separate the sensor into two connectable portions; a sensor head and a sensor body, which contains the remaining subcomponents. The sensor head contains a minimal amount of complexity and is typically designed in such a way so as to be able to withstand radiation or high temperature. The sensor body includes the electronics required to control the inputs to the sensor field and to convert the output from the sensor head into a meaningful result. These two components are typically connected via leads, such as wires, and are connected after the sterilization process is completed.

The use of SOI technology allows for much improved and more convenient implementation of electronics in sterilized pharmaceutical components. For example, in some embodiments, the sensor head is very sensitive and requires individualized calibration to insure proper readings. For example, an analog output from a sensor head may be related to the temperature by a particular equation, wherein the coefficients of that equation are unique to the sensor head. By calibrating the sensor head and storing those values proximate to the sensor head, the sensor head can now be used with a generic sensor body without any additional calibration required. Storing these calibration values proximate to the sensor head requires that the storage device be capable of withstanding some type of sterilization process. Memories manufactured using the SOI technologies can be integrated into the sensor head, allowing calibrated sensors to be employed.

In a second embodiment, the sensor head and sensor body are incorporated into a single self-contained component. This self-contained sensor includes the previously described sensor head. As described above, it also includes a power conversion/generation circuit, which generates power for the device, preferably from radiated electromagnetic fields. The sensor also includes the circuitry necessary to convert the analog output from the sensor head into a digital value, the logic required to convert that value to an appropriate computer usable result, and a transmitter to deliver that result, preferably wirelessly to an external device. If all of these components are manufactured using SOI, the entire sensor can be sterilized without fear of damage or degradation.

Figure 6A:
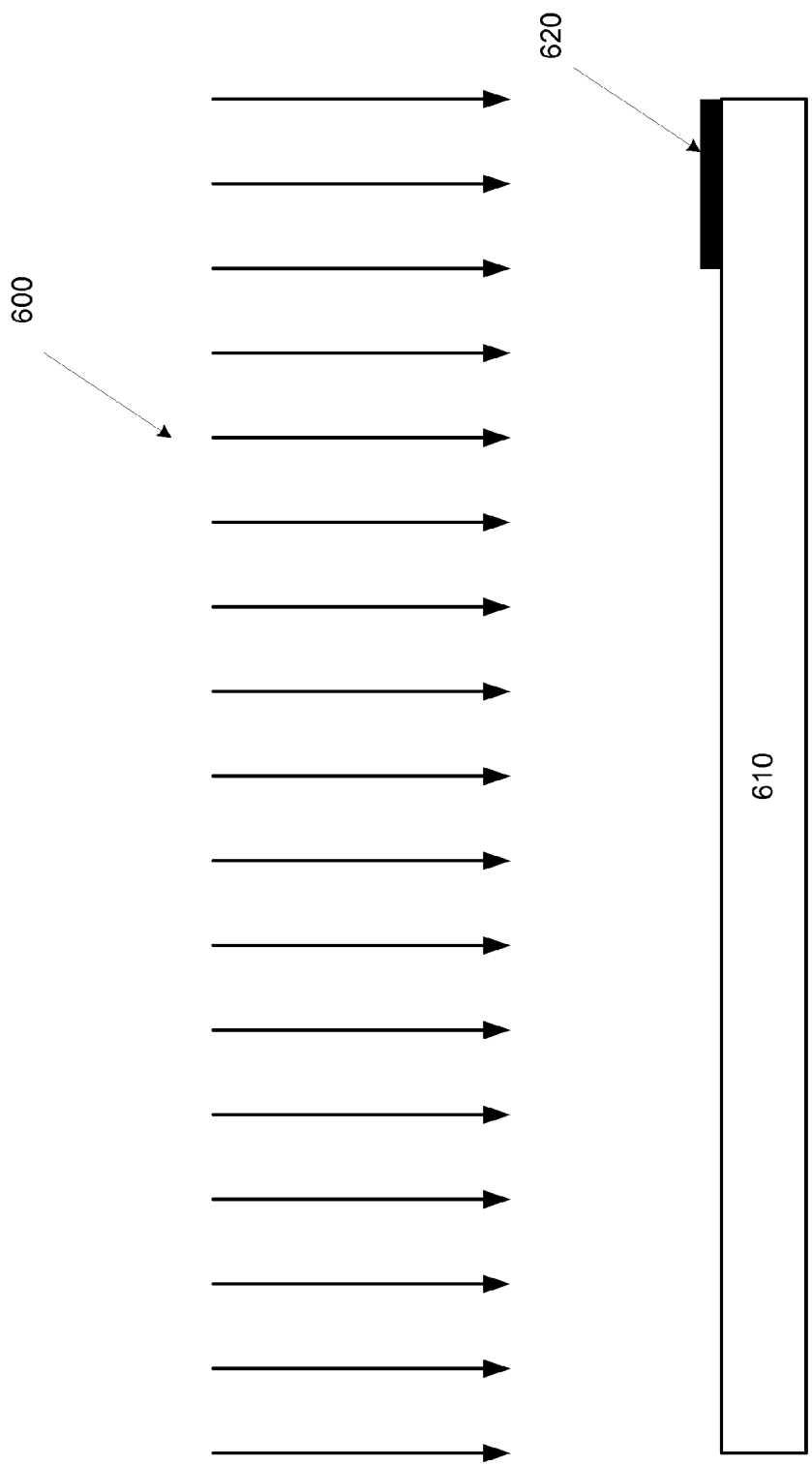
FIG. 6a shows one orientation of a bag and attached semiconductor.

As mentioned above, electronic devices using SOI technology can withstand gamma or beta radiation. To increase the amount of radiation that the electronic device can withstand, it may be possible to change the orientation of the device during the sterilization process. Typically, gamma rays are directed predominantly along one axis. For example, assume that the gamma rays are moving in the Z axis. Typically, the item to be sterilized, such as a pharmaceutical bag, is placed such that its maximum surface area is positioned perpendicular to the flow of gamma rays. FIG. 6a shows gamma rays 600 flowing in the Z axis. The item to be sterilized 610 and the attached semiconductor device 620 are positioned so as to maximize the surface area impacted by the gamma rays 600. While this orientation is best for the item to be sterilized 610, it subjects the semiconductor device 620 to high levels of radiation.

To reduce these levels of radiation, the semiconductor device 620 can be oriented such that its cross-section (as viewed in FIG. 3) is perpendicular to the flow of gamma rays (such as in the XY plane). Stated another way, the maximum surface area of the semiconductor device 620 is oriented so as to be coplanar to the direction of the gamma rays, as shown in FIG. 6b. In this way, a minimal surface area is susceptible to being impacted by the rays. Other orientations are also possible, where the cross-sectional exposure of the electronic device is not at its maximum. However, the item to be sterilized 610 still exposes a large cross-section to the gamma rays 600.

Figure 7:
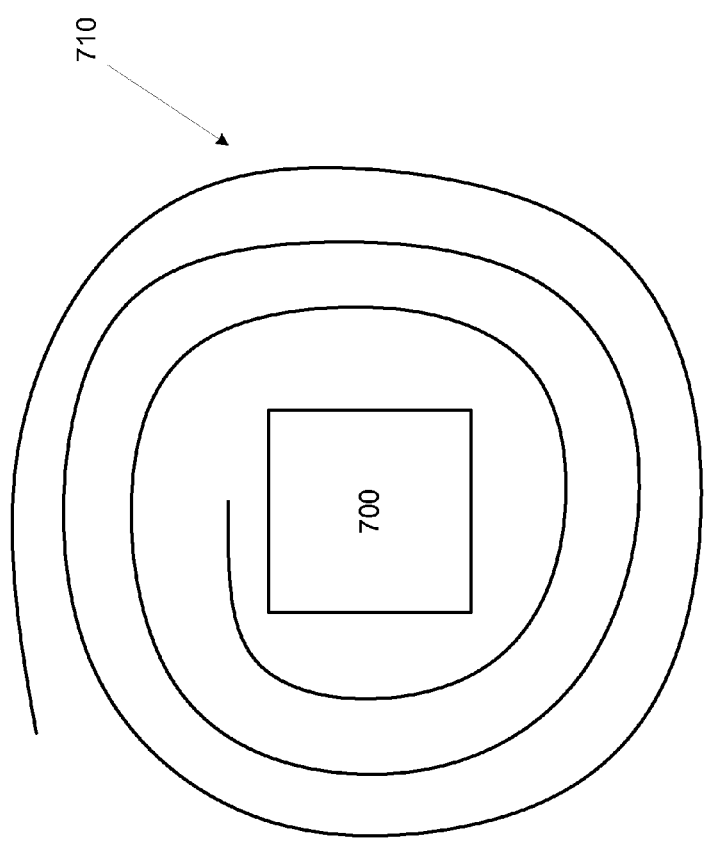
FIG. 7 shows a heater used with a SOI substrate in accordance with one embodiment.

Other techniques may also be used to reduce the effect of gamma or beta radiation on these electronic devices. In some embodiments, a SOI device may be temporarily disabled or affected by the exposure to radiation. Reconditioning, by applying heat or simply allowing time to elapse, may be an effective method to restore the functionality of the device. In one embodiment, after the device is sterilized, it is not used for a predetermined period of time to allow it to recondition itself. In a second embodiment, after the electronic device is sterilized, it is subjected to heat to recondition it. In a further embodiment, a small heater may be installed near the semiconductor device that can be activated after exposure to radiation. FIG. 7 shows an example of such a heater 710. For example, the heater 710 may consist of a small coil oriented around the semiconductor device 700. The coil can receive induced electromagnetic waves, which it then converts to current. This current is used to create heat, which is used to recondition the semiconductor device 700. After exposure to radiation, this heater 710 can be activated, which supplies localized heat to the semiconductor device 700, allowing it to recondition itself.

In addition to the benefit of withstanding sterilization, these semiconductor devices can also operate at high temperature ranges. Therefore, it is also possible to have these sensors functional during a high temperature steam sterilization procedure. Thus, in situ temperature measurements can be made during sterilization or autoclaving, which allows the operator to verify that the sterilization temperature ranges and profiles conform to required values. In contrast, the actual temperature profile of a hot steam sterilization cycle currently cannot be monitored in situ.

In addition to withstanding high temperatures, it is also believed that SOI technology is more tolerant of extremely low temperatures, such as much less than −55° C. The ability of a semiconductor material to conduct is proportional to the dopant level and the base energy level, or thermal state. Typically semiconductor devices are doped to operate within the common industrial temperatures, −55 to +85 C. Increasing the temperature of the semiconductor device will increase the ability for the device to conduct or change states. However, at lower temperatures, the energy required to excite the transistor may exceed the maximum input energy and therefore standard devices will not operate reliably below −55° C. SOI can more reliably operate at lower temperatures than standard semiconductor devices because less input energy is lost to parasitic leakage to adjacent devices.

This feature can also be advantageously exploited by pharmaceutical components. For example, many pharmaceutical products are stored in sub-freezing environments. Furthermore, the temperature profile of the drug as it is being frozen is critical to maintaining the proper molecular and crystalline structure. A temperature sensor that is able to operate at these frigid temperatures would allow the operator to monitor the temperature as the product is being frozen to verify that the proper temperature profile was followed.

In one embodiment, the temperature sensor records the temperature at fixed intervals and stores these values in an internal memory. At a later time, these stored values can be retrieved by an external device that compares the stored values to acceptable temperature profiles. In another embodiment, the temperature sensor transmits these values to an external device, which monitors the temperature of the product as it is being frozen. The transmission can be by wire or wirelessly as described above. The external device can then insure that a proper temperature profile was followed.

This procedure is not possible today. Rather, freezers are calibrated and then products frozen in that freezer unit are assumed to have followed the profile exhibited during calibration. Therefore, this new approach would allow the operator to insure that each product was subjected to a proper freezing profile, since the temperature versus time data would be attainable for each individual product.

Similarly, this technique can be used to monitor and verify the thawing process. As the frozen product is thawed, its temperature can be recorded by the temperature sensor, as described above. The thawing continues until the product reaches its desired use temperature. The collected temperature values can then be compared to a proper or acceptable temperature profile to insure the quality of the product.

This technique can also be used to calibrate the freezing profile of the freezer itself. For example, a freezer is calibrated using thermocouple wires that are thread into the interior. Due to the freezers design with insulation and sealed enclosure, routing the thermocouples to the preferred locations within the interior can be complicated and time consuming. A device that can wireless communicate through the closure or portals of the freezer may be used to allow temperature to be measured with the enclosure.

Silicon on Insulator (SOI) technology is also believed to be more resistant to magnetic fields, especially alternating magnetic fields. This is believed to be true for several reasons. First, SOI transistors can hold their state more effectively and efficiently to reduce the effects of induced currents from the AC field. Second, SOI transistors have less leakage, therefore they will be less susceptible to draining the transistors in an excited state. Such an environment may be encountered in various applications, For example, in the pharmaceutical industry, magnetically levitated mixer heads are often used, such as in the MOBIUS® Mix 100, 200 and 500 disposable mixer systems available from Millipore Corporation of Billerica, Mass. These systems use a magnetic drive on the outside of the mixing container to remotely drive a magnetic impeller within the container in order to mix its contents either as a straight industrial mixer or as a bioreactor. The use of SOI technology will allow electronics to be placed in closer proximity to this magnetic field source.

Perhaps the most interesting application of this technology is in disposable products for the biopharmaceutical or medical industry where one or more of these conditions are used on the same product over its life time. Having electronics that are capable of working in any or all of these conditions would be exceedingly useful to the operator. For example, a sample bag used on a disposable bioreactor, can have one or more electronic devices, for example a RFID or other wireless communication and memory storage device. One such system is taught by copending application WO 2009/017612. Having electronics of the SOI type, one can form the sampler bag and attach a wireless communications and memory device and then gamma or beta sterilize it for shipping, storage and use by the customer. Data relating to the lot number, date of manufacture, use restrictions and the like can be safely added before gamma or beta sterilization and read after gamma or beta sterilization. One or more trackable events such as the date of use, the location of use, operator, sample taken etc can be added to the memory by the user as a paperless record keeping system and may interface with its Good Manufacturing or Good Laboratory practices systems such as a LIMS systems. The sample may then be frozen as a retain and the SOI based electronics will allow it to be safely stored at those temperatures and thawed at a later date with its memory and stored data intact.

Similar applications apply to the medical field where blood or other components can be added to gamma or beta sterilized containers and stored at low temperatures until needed. Likewise, retains or medical samples such as biopsies could be handled in the same manner and yield the same satisfactory results.

What is claimed:

1. A method of creating a sterile component, having embedded electronics, comprising:
    manufacturing an electronic device using Silicon on Insulator (SOI) technology;
    affixing said electronic device to said component;
    sterilizing said component by subjecting said component to gamma or beta radiation;
    attaching a heater near said electronic device, wherein said heater comprises a coil oriented around said electronic device; and
    reconditioning said electronic device after exposure to said radiation by activating said heater.

2. The method of claim 1, wherein said component is selected from the group consisting of filters, bags, tubes and process instruments.

3. The method of claim 1, wherein said electronic device comprises wireless communication means.

4. The method of claim 3, wherein said means comprises RFID.

5. The method of claim 3, wherein said means comprises the communication protocol described in IEEE 802.15.4.

6. The method of claim 3, wherein said means comprises the communication protocol described in IEEE 802.15.1.

7. The method of claim 1, wherein said electronic device is a sensor adapted to convert a physical characteristic to an electric signal, selected from the group consisting of fluid condition sensors, including pressure sensors, temperature sensors, and flow rate sensors, and fluid component sensors, including chemical sensors and concentration sensors.

8. The method of claim 7, wherein said sensor comprises a sensor head, and said sensor head is manufactured using SOI technology.

9. The method of claim 7, wherein said sensor comprises a signal processing unit, and said signal processing unit is manufactured using SOI technology.

10. The method of claim 1, wherein said radiation is transmitted substantially along one direction, and said electronic device is oriented so as not to maximize its surface area exposed to said radiation.

* * * * *